United States Patent
Guzman Sanchez et al.

(10) Patent No.: US 9,532,786 B2
(45) Date of Patent: Jan. 3, 2017

(54) COMPRESSIVE SYSTEM FOR REDUCING EDGE BLEEDING IN CLASSICAL HYSTEROTOMY IN CASES OF PLACENTA PRAEVIA

(71) Applicants: Arnoldo Guzman Sanchez, Jalisco (MX); Eduardo Rodriguez de Anda, Jalisco (MX)

(72) Inventors: Arnoldo Guzman Sanchez, Jalisco (MX); Eduardo Rodriguez de Anda, Jalisco (MX)

( * ) Notice: Subject to any disclaimer, the term of this patent is extended or adjusted under 35 U.S.C. 154(b) by 151 days.

(21) Appl. No.: 14/394,340

(22) PCT Filed: Mar. 15, 2013

(86) PCT No.: PCT/MX2013/000032
§ 371 (c)(1),
(2) Date: Oct. 14, 2014

(87) PCT Pub. No.: WO2013/157913
PCT Pub. Date: Oct. 24, 2013

(65) Prior Publication Data
US 2015/0088173 A1    Mar. 26, 2015

(30) Foreign Application Priority Data
Apr. 17, 2012 (MX) .................. MX/A/2012/004494

(51) Int. Cl.
*A61B 17/42* (2006.01)
*A61B 17/122* (2006.01)

(52) U.S. Cl.
CPC ........... *A61B 17/1227* (2013.01); *A61B 17/42* (2013.01)

(58) Field of Classification Search
CPC ... A61B 17/10; A61B 17/122; A61B 17/1227; A61B 17/128; A61B 17/28; A61B 17/2804; A61B 17/2816; A61B 17/282; A61B 17/2833; A61B 17/2841; A61B 17/42; A61B 17/44; A61B 2017/2845; A61F 6/206
See application file for complete search history.

(56) References Cited

U.S. PATENT DOCUMENTS 2,890,519 A * 6/1959 Storz, Jr. ............. A61B 17/128 29/225
3,326,217 A * 6/1967 Kerr ................... A61B 17/1227 24/513

(Continued)

FOREIGN PATENT DOCUMENTS

| EP | 2404562 | 1/2012 |
| WO | WO02/02014 | 1/2002 |
| WO | WO2006/049960 | 5/2006 |

*Primary Examiner* — Ryan J Severson
(74) *Attorney, Agent, or Firm* — Defillo & Associates, Inc; Evelyn A Defillo

(57) ABSTRACT

The invention relates to a compressive system for reducing edge bleeding in classical hysterotomy in cases of placenta praevia, said system comprising: a compressive device formed by two compressive bars and bracketing members; and a clamp for applying the compressive device, said clamp comprising two handles, two jaws, a rotation nut, two protuberances and a threaded adjustment nut. The clamp allows the opening of the compressive bars. The device is applied to the edges of the hysterotomy and, subsequently, the clamp is withdrawn.

3 Claims, 3 Drawing Sheets

(56) References Cited

U.S. PATENT DOCUMENTS

| | | | | |
|---|---|---|---|---|
| 3,575,405 A * | 4/1971 | Harding | ............... | B25B 5/106 269/211 |
| 3,604,425 A * | 9/1971 | Le Roy | ............... | A61B 17/1227 24/562 |
| 3,802,437 A * | 4/1974 | Kees, Jr. | ............... | A61B 17/1227 24/510 |
| 3,805,792 A * | 4/1974 | Cogley | ............... | A61B 17/1227 606/142 |
| 4,051,844 A * | 10/1977 | Chiulli | ............... | A61B 17/02 600/217 |
| 4,112,951 A * | 9/1978 | Hulka | ............... | A61B 17/282 128/831 |
| 4,555,100 A * | 11/1985 | Ditto | ............... | B25B 5/02 269/166 |
| 4,706,668 A * | 11/1987 | Backer | ............... | A61B 17/1285 606/142 |
| 4,777,949 A * | 10/1988 | Perlin | ............... | A61B 17/1227 24/546 |
| 4,932,955 A * | 6/1990 | Merz | ............... | A61B 17/1227 24/510 |
| 5,104,397 A * | 4/1992 | Vasconcelos | ............... | B25B 7/14 606/206 |
| 5,304,183 A * | 4/1994 | Gourlay | ............... | A61B 17/00234 227/901 |
| 5,368,600 A * | 11/1994 | Failla | ............... | A61B 17/1285 606/139 |
| 7,322,995 B2 * | 1/2008 | Buckman | ............... | A61B 17/08 24/499 |
| 7,648,514 B1 * | 1/2010 | Nakao | ............... | A61B 17/064 227/175.1 |
| 7,651,511 B2 * | 1/2010 | Burbank | ............... | A61B 8/06 606/158 |
| 7,842,045 B2 * | 11/2010 | Vandenbroek | ............... | A61B 17/128 606/142 |
| 8,187,290 B2 * | 5/2012 | Buckman | ............... | A61B 17/08 606/157 |
| 8,864,775 B2 * | 10/2014 | Lazic | ............... | A61B 17/1227 606/139 |
| 2004/0153097 A1 * | 8/2004 | Burbank | ............... | A61B 17/12 606/119 |
| 2005/0101974 A1 * | 5/2005 | Burbank | ............... | A61B 8/06 606/151 |
| 2005/0113634 A1 | 5/2005 | Burbank et al. | | |
| 2008/0188863 A1 * | 8/2008 | Chu | ............... | A61B 17/12 606/119 |
| 2011/0251622 A1 * | 10/2011 | Basic | ............... | A61B 17/12 606/119 |
| 2014/0336683 A1 * | 11/2014 | Guzman Sanchez | | A61B 17/122 606/158 |
| 2015/0025542 A1 * | 1/2015 | Guzman Sanchez | .. | A61B 17/42 606/119 |
| 2015/0088173 A1 * | 3/2015 | Guzman Sanchez | .. | A61B 17/42 606/158 |

\* cited by examiner

COMPRESSIVE SYSTEM FOR REDUCING EDGE BLEEDING IN CLASSICAL HYSTEROTOMY IN CASES OF PLACENTA PRAEVIA

CROSS REFERENCE TO RELATED APPLICATION

This application is a national stage entry of PCT/MX2013/000032 filed Mar. 15, 2013, under the International Convention, claiming priority over Mexican Patent Application No. MX/a/2012/004494 filed Apr. 17, 2012.

TECHNICAL FIELD

The present invention relates to a surgical system that reduces the bleeding that occurs in the edges region of a classical hysterotomy (cut made in the matrix) during the caesarean practiced because of placenta praevia. The bleeding reduction is due to the compressive of the edges of the hysterotomy. This system comprises essentially a compressive device and its corresponding application clamp.

BACKGROUND OF THE INVENTION

There is not a specific tool that compresses the edges that are generated by a classical hysterotomy during a cesarean practiced due to placenta praevia. Although there is a clamp called Allis clamp (see FIG. 1), the latter has an oppressive part that is very small, which occludes an equally small section of the edges of the hysterotomy, in this place there are blood vessels that have a large diameter, leaving them only partially occluded; also because the hysterotomy edges are too thick, the pressure exerted by the Allis clamp is limited. Also, this clamp is too long and is technically difficult to suture the edges of the hysterotomy and also requires an exaggerated number of clamps in this type of surgery.

SUMMARY OF THE INVENTION

On the contrary, the present invention achieves the hermetic occlusion of a very broad surface of the edges of the hysterotomy, in addition a predetermined compressive is achieved, thus does not require any adjustment by the person applying the device. In addition, its size and design allow easy access for the surgical maneuvers and for performing the suture of the uterine tissue. Therefore, the reduction in bleeding is achieved decreasing the required surgical instruments, compared to traditionally used Allis clamp.

From the use of this device, 80 to 90% of the bleeding has been reduced that occurred at the edges of the hysterotomy.

Problem to Solve

Reduce the maternal death by bleeding.

The World Health Organization blames maternal bleeding as the leading cause of maternal mortality in Latin America, which is a tragedy.

The World Health Organization's fifth objective literally states, "maternal death should be reduced"; objective that must be attained.

How to Solve the Problem

The bleeding problem from the area of the hysterotomy, of which we refer to, has been solved by using the aforementioned compressive system for reducing the bleeding of the classical hysterotomy; instrument that is designed for use in placenta praevia. This system blocks 80 to 90% of the blood flow in the edges of the hysterotomy.

The experience with performing 75 surgeries, in which were applied the compressive system of the present invention to reduce the bleeding of the classical hysterotomy for use in placenta praevia, demonstrates the utility of this device.

The present invention relates to a compressive system to reduce bleeding on edges of a hysterotomy in placenta praevia, the system comprising: a compressive device having compressive bars connected by brackets; and a clamp; each one of the compressive bars including a first end, a second end, a bridge, and a longitudinal face having a plurality of teeth having pointed ends; the compressive bars are placed one against the other by the longitudinal faces; the bridge includes a first hole and a second hole; the first end and the second end of the compressive bars have a threaded hole; each one of the brackets includes a first bar, a second bar, and springs; each one of the first bar and the second bar include a hole on a first end and a drilled base on a second end, the first and second bars are connected by placing a bolt through the holes; each one of the drilled bases include a perforation, the drilled bases are connected to the compressive bars by placing a screw through the perforations and the threaded hole of the corresponding compressive bar; each spring has a first end connected to the first bar and a second end connected to the second bar; the clamp includes a handle, a jaw, and a threaded adjustment bolt; the handle and the jaw are connected by a rotation pin; the jaw includes an outer section having a protrusion, each protrusion is connected to the corresponding bridge; and the clamp is designed to allow the compressive device to be placed on the edges of the hysterotomy to reduce bleeding.

DETAILED DESCRIPTION OF THE INVENTION

The present invention provides a compressive system for reducing the bleeding originated on the edges to the classical hysterotomy for the placenta praevia cases.

Figure 1:
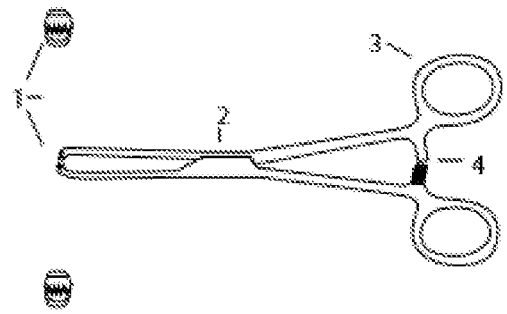
FIG. 1 shows an Allis clamp.

As can be seen in FIG. 1, the Allis clamp includes Element (1): Clamp tip, characterized by having small slits in each of the arms; Element (2): rotation axis, which allows the opening or closing of the arms of the clamps; Element (3) clamping rings and control of the opening and closing of the arms of the clamps; and Element (4) clamping and adjusting pressure slits of the clamp tip.

Figure 2:
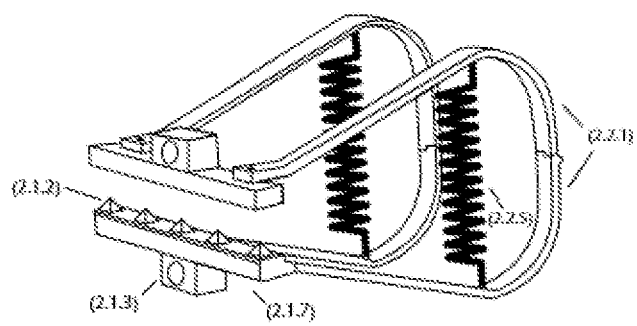
FIG. 2 shows the compressive device according to the present invention.
Figure 2:
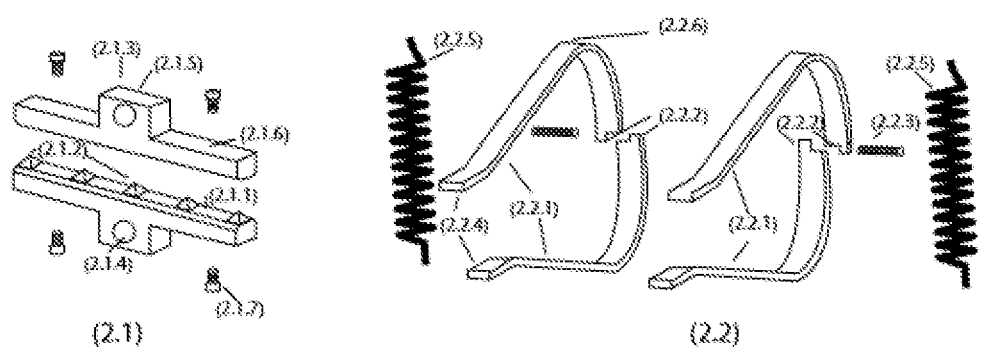

FIG. 2 shows the compressive device according to the present invention. The compressive device comprises: A) The compressive bars (2.1), these have a longitudinal face (2.1.1) with a series of teeth (2.1.2) and also a bridge (2.1.3) that has a first hole (2.1.4) and a second hole (2.1.5), also has threaded holes (2.1.6) and screw-studs (2.1.7). B) Brackets (2.2) which have bars (2.2.1), holes (2.2.2), pins (2.2.3), drilled bases (2.2.4), springs (2.2.5) and the holes (2.2.6).

Figure 3:
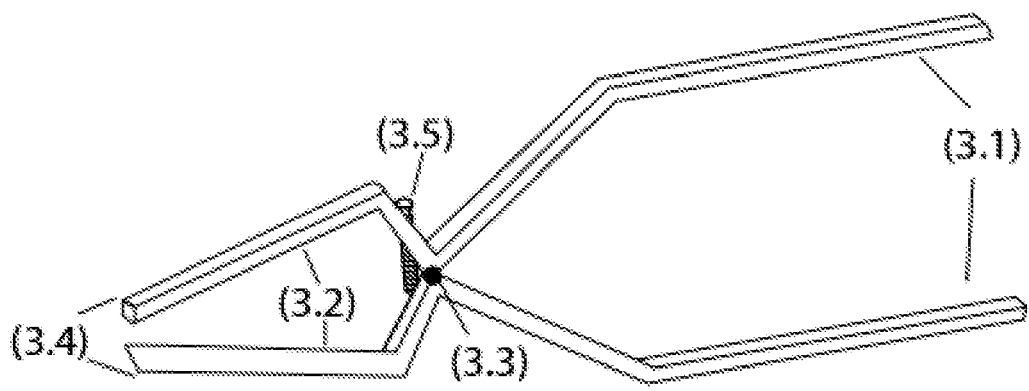
FIG. 3 shows an application clamp for the compressive device according to the present invention.

FIG. 3 shows an application clamp for the compressive device, according to the present invention The clamp comprises: The handles (3.1), the jaws (3.2), the rotation pin (3.3), protrusions (3.4) and the threaded adjustment bolt (3.5).

Figure 4:
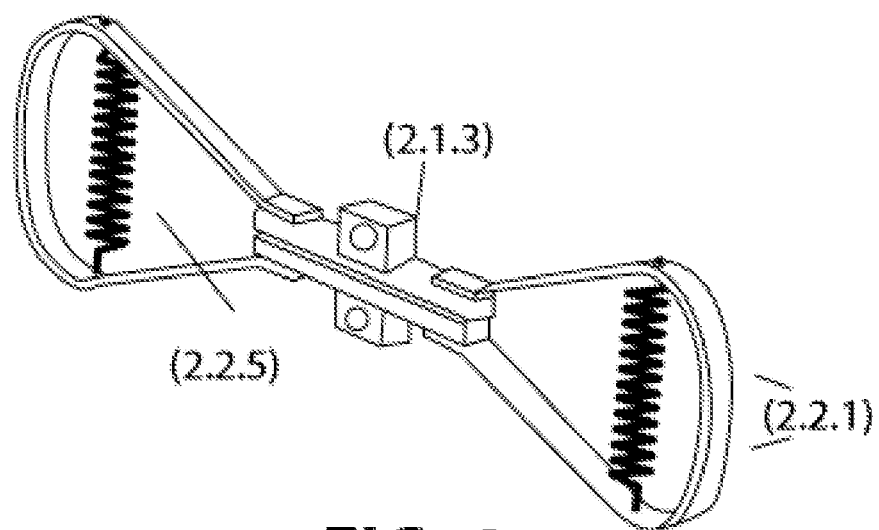
FIG. 4, shows the compressive device with the brackets (2.2) longitudinally oriented to the compressive bars (2.1)

FIG. 4 shows the compressive device with the brackets (2.2) longitudinally oriented to the compressive bars (2.1).

Figure 5:
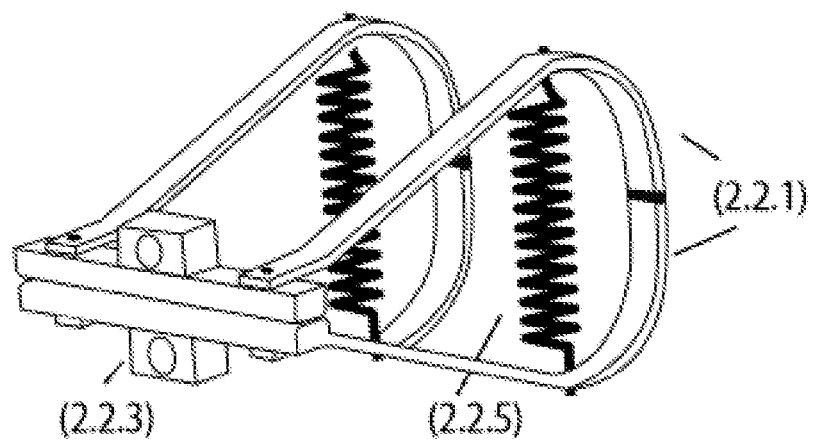
FIG. 5 shows the compressive device with both brackets (2.2) at right angles with respect to the compressive bars (2.1) on the same side, in relation to compressive bars.

FIG. 5 shows the compressive device with both brackets (2.2) at right angles with respect to the compressive bars (2.1) on the same side, in relation to compressive bars.

Figure 6:
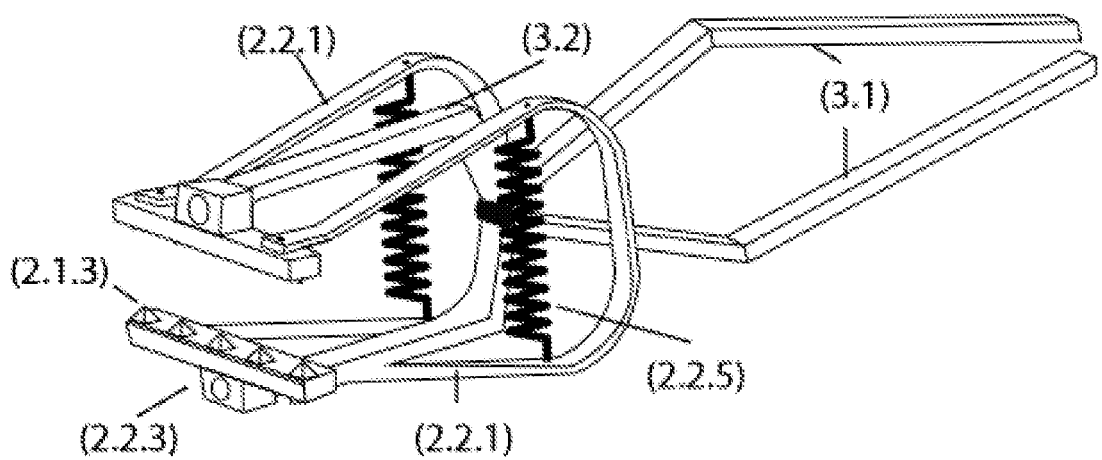
FIG. 6 shows the application clamp (FIG. 3) and the compressive device (FIG. 2), both devices are shown on how to be coupled prior to their placement on the edge of the hysterotomy (cut made in the matrix).

FIG. 6 shows the application clamp (FIG. 3) and the compressive device (FIG. 2), both devices are shown on how to be coupled prior to their placement on the edge of the hysterotomy (cut made in the matrix).

The elements of the compressive system are:
1. Compressive device. See FIG. 2.
2. Application clamp for the compressive device. See FIG. 3.

1. Compressive device, see FIG. 2. Comprises two sections: a) the compressive bars (2.1) and b) the brackets (2.2).

A) The compressive bars (2.1) are two solid bars that are placed against one another by one of its longitudinal faces (2.1.1). On each of the longitudinal faces (2.1.1) is a series of teeth (2.1.2) with pointed ends whose function is partly to penetrate the tissue of the edges of the hysterotomy. This series of teeth (2.1.2) prevent the sliding of the compressive bars (2.1). The central part of the compressive bars (2.1) includes a machined bridge (2.1.3) located on the opposite sides of both longitudinal faces (2.1.1). The bridge has two holes, a first hole (2.1.4) and the second hole (2.1.5) which is perpendicular to the first hole (2.1.4).

Each of the ends of the compressive bars (2.1), includes a threaded hole (2.1.6), located on the same side where the bridge is machined (2.1.3). In each threaded hole (2.1.6) a screw stud (2.1.7) is screwed.

B) Brackets (2.2). The brackets (2.2) are two. Each one comprises two bars (2.2.1). Each bar has one end of its ends a machined hole (2.2.2) that is used to join to the other bar by a bolt (2.2.3) which functions as an axis of rotation, and at the two opposite ends of both bars (2.2.1), there is a drilled base (2.2.4), both bars are designed to permit the placement of a spring (2.2.5) which is fixed in the holes (2.2.6) of the two bars. The spring (2.2.5) is placed at close distance to the pin (2.2.3). The magnitude of the compressive force is in accordance with the mechanical properties of the material of the spring (2.2.5).

Both brackets (2.2) are connected to the compressive bars (2.1), through the section of the element called the drilled base (2.2.4), through this drilled base (2.2.4) the screw-bolt (2.1.7) is passed, which is screwed into the threaded hole (2.1.6) of the compressive bars (2.1).

Likewise, the spring (2.2.5) may be replaced by any other element a provides the compressive force, such as screws, arcs, polymers, etc.

The number of brackets (2.2) may change depending on the desired compressive force. 2-. Application clamp for the compressive device, see FIG. 3. The clamp has two sections: A) the handle (3.1), and B) the jaw (3.2). Both sections are connected by a rotation pin (3.3). On the outside part of the tips of the jaw, a protrusion (3.4) is machined which is adapted to the bridge (2.1.3) located on the opposite side of the longitudinal face (2.1.1) of the compressive bars (2.1). The application clamp for the compressive devices, FIG. 3, allows the opening of the compressive bars (2.1). This way allows to place the compressive device, FIG. 2, to the hysterotomy to reduce bleeding as was previously indicated.

A threaded adjustment bolt (3.5) which is close to the rotation pin (3.3) allows to adjust the initial opening of the application clamp for the compressive device, FIG. 3, to facilitate the entrapment of the bridges (2.1.3) of both bars compressive (2.1) when the compressive device, FIG. 2, has not yet been applied to the hysterotomy.

Also, allows a thickness reduction of the bridge (2.1.3), or any other configuration that allows the entrapment of the protrusion (3.4) with the bridge (2.1.3).

Integral mechanism of operation of the compressive system to reduce the bleeding in the edges of the classical hysterotomy for cases of placenta praevia:

The compressive system comprises: A. a compressive device, FIG. 2, and B. application clamp for the compressive device, FIG. 3. The compressive system works as follows:

a) Before use, the compressive device, FIG. 2, has the compressive bars (2.1) strongly linked through the springs (2.2.5). Furthermore, before using the compressive device normally has the brackets longitudinally oriented to the compressive bars, as shown in FIG. 4.

b) To apply the compressive device, FIG. 2, both brackets must be at right angles with respect to the compressive bars (2.1) and both brackets must also be on the same side, relative to the compressive bars, FIG. 5.

c) Application of compressive device, FIG. 2, is made by adapting the protrusions (3.4) of the application clamp for the compressive device, FIG. 3, to the bridges (2.1.3) of both compressive bars (2.1). Then, the two arms of the handle (3.1) are approximated to thereby separate the compressive bars (2.1) and are applied to the edges of the hysterotomy, see FIG. 6.

d) Once the compressive device, FIG. 2, is applied to the edges of the hysterotomy, the application clamp of the compressive device is removed, FIG. 3, which allows the compression of the edges of the hysterotomy, to stop the bleeding.

e) Upon completion of the surgical procedures the compressive devices, FIG. 2, are removed.

The claims are based on the fundamental problem of bleeding in placenta praevia, which is a serious complication that occurs during a caesarean section, to which the present device offers an alternative solution to reduce the bleeding of the hysterotomy for a classic cesarean section; for which an extensive experience in Fray Antonio Alcalde Civil Hospital of Guadalajara, Jalisco.

Having described my invention, as above, I consider it as a novelty and claim my property in the following claims:

1. A compressive system to reduce bleeding on edges of a hysterotomy in placenta praevia, the system comprising:
   a compressive device having compressive bars connected by brackets; and
   a clamp;
   each one of the compressive bars including a first end, a second end, a bridge, and a longitudinal face having a plurality of teeth having pointed ends;
   the compressive bars are placed one against the other by the longitudinal faces;
   the bridge includes a first hole and a second hole;
   the first end and the second end of the compressive bars have a threaded hole;

each one of the brackets includes a first bar, a second bar, and springs;

each one of the first bar and the second bar include a hole on a first end and a drilled base on a second end, the first and second bars are connected by placing a bolt through the holes;

each one of the drilled bases include a perforation, the drilled bases are connected to the compressive bars by placing a screw through the perforations and the threaded hole of the corresponding compressive bar;

each spring has a first end connected to the first bar and a second end connected to the second bar;

the clamp includes a handle, a jaw, and a threaded adjustment bolt;

the handle and the jaw are connected by a rotation pin;

the jaw includes an outer section having a protrusion, each protrusion is connected to the corresponding bridge;

the clamp is designed to allow the compressive device to be placed on the edges of the hysterotomy to reduce bleeding.

2. The compressive system according to claim 1, wherein the spring is selected from the group consisting of a compressive force device, screws, arcs, and polymers.

3. The compressive system according to claim 1, wherein the first bar and the second bar have a curvature.

* * * * *